United States Patent [19]
Takao

[11] Patent Number: 4,736,053
[45] Date of Patent: Apr. 5, 1988

[54] PHOSPHORIC ESTER DERIVATIVES AND INSECTICIDAL AND MITICIDAL COMPOSITIONS CONTAINING SAID DERIVATIVES

[75] Inventor: Hisashi Takao, Tokushima, Japan

[73] Assignee: Otsuka Kagaku Kabushiki Kaisha, Osaka, Japan

[21] Appl. No.: 3,430

[22] Filed: Jan. 15, 1987

[30] Foreign Application Priority Data

Jan. 22, 1986 [JP] Japan ............... 61-12849
Dec. 5, 1986 [JP] Japan ............... 61-291269

[51] Int. Cl.⁴ .................................. C07F 9/165
[52] U.S. Cl. .......................... 558/197; 558/210
[58] Field of Search ............... 558/197, 210; 514/130, 514/128, 147

[56] References Cited

U.S. PATENT DOCUMENTS 3,839,509 10/1974 Drabek et al. ............ 558/210
3,879,499 4/1975 Beriger et al. ............ 558/210
4,457,922 7/1984 Wilson, II ................ 558/162

OTHER PUBLICATIONS

Chemical Abstract 101:130897n.

*Primary Examiner*—Anton H. Sutto
*Attorney, Agent, or Firm*—Armstrong, Nikaido, Marmelstein & Kubovcik

[57] ABSTRACT

Disclosed are novel phosphoric ester derivatives of the formula (I):

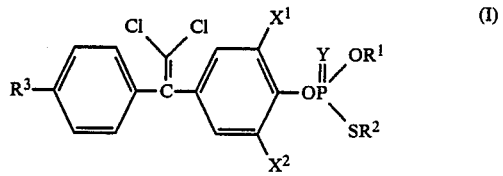

wherein $R^1$ and $R^2$ each represents a lower alkyl group; $R^3$ represents a hydrogen atom, a halogen atom, a lower alkyl group, a lower alkoxy group or a lower alkylthio group; $X^1$ and $X^2$ are the same or different and each represents a hydrogen atom or a halogen atom; and Y represents an oxygen atom or a sulfur atom, and insecticidal and miticidal compositions containing said derivatives.

2 Claims, No Drawings

PHOSPHORIC ESTER DERIVATIVES AND INSECTICIDAL AND MITICIDAL COMPOSITIONS CONTAINING SAID DERIVATIVES

The present invention relates to novel phosphoric ester derivatives and insecticidal and miticidal compositions containing said derivatives.

There are compounds having miticidal activity among the organic phosphoric acid derivatives heretofore known. However, these compounds have potent insecticidal activity as well, and as they exhibit strong killing effects on insects of the order Coleoptera including ladybugs which are the natural enemies of mites, these known compounds inevitably exterminate such natural enemies of mites as well, thus being poor in selectivity of action. Furthermore, these compounds are inadequate in residual miticidal action and are highly toxic to warm-blooded animals. It is for this reason that none of the hitherto-known organic phosphoric ester derivatives has been commercially developed as a miticidal agent.

It is, therefore, an object of the present invention to provide an insecticidal and miticidal compound which does not eradicate natural enemies of mites but has insecticidal activity against other harmful insects.

It is another object of the present invention to provide an insecticidal and miticidal composition containing the above-mentioned compound.

In accordance with the present invention, there are provided novel phosphoric ester derivatives of the formula (I):

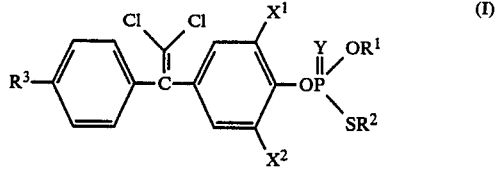

wherein $R^1$ and $R^2$ each represents a lower alkyl group; $R^3$ represents a hydrogen atom, a halogen atom, a lower alkyl group, a lower alkoxy group or a lower alkylthio group; $X^1$ and $X^2$ are the same or different and each represents a hydrogen atom or a halogen atom; and Y represents an oxygen atom or a sulfur atom.

In accordance with the present invention, there is further provided an insecticidal and miticidal composition comprising an effective amount of at least one species of the phosphoric ester derivative of the formula:

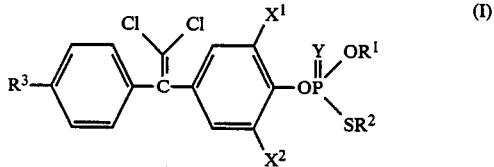

wherein $R^1$ and $R^2$ each represents a lower alkyl group; $R^3$ represents a hydrogen atom, a halogen atom, a lower alkyl group, a lower alkoxy group or a lower alkylthio group; $X^1$ and $X^2$ are the same or different and each represents a hydrogen atom or a halogen atom; and Y represents an oxygen atom or a sulfur atom, and a vehicle, diluent or carrier therefor.

In the course of development studies on compounds that might be implemented as insecticides and miticides, the present inventors discovered that a phosphoric ester derivative of the above formula (I) has exceedingly high miticidal activity and insecticidal activity against noxious insects such as those of the orders Lepidoptera, Hemiptera and Thysanoptera without displaying terminating effects on natural enemies of mites, that the duration of such activities is long, that it has only very low toxicity to warm-blooded animals so that it can be advantageously utilized as an insecticidal and miticidal agent. The present invention has been accomplished on the basis of the above findings.

In this specification and the claims appended thereto, particularly referring to the formulas given therein, $R^1$, $R^2$, $R^3$, $X^1$ and $X^2$ specifically mean the following.

The lower alkyl group includes $C_{1-6}$ alkyl groups such as methyl, ethyl, n-propyl, isopropyl, n-butyl, isobutyl, sec-butyl, amyl, hexyl and so on.

The lower alkoxy group includes $C_{1-4}$ alkoxy groups such as methoxy, ethoxy, n-propoxy, isopropyloxy, n-butoxy, isobutyloxy, sec-butyloxy, and so on.

The lower alkylthio group includes $C_{1-6}$ alkylthio groups such as methylthio, ethylthio, n-propylthio, isopropylthio, n-butylthio, isobutylthio, sec-butylthio, n-hexylthio and so on.

The halogen atom may for example be chlorine, bromine or the like.

The phosphoric ester derivative of the formula (I) can be produced by various methods. Typically, the method represented by the following reaction scheme 1 may be employed.

REACTION SCHEME 1

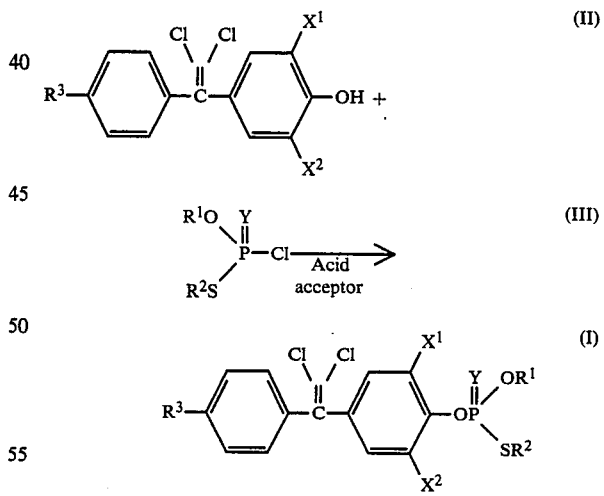

In the foregoing formulas, $R^1$, $R^2$, $R^3$, Y, $X^1$ and $X^2$ are as defined hereinbefore. Thus, the compound of the present invention is produced by reacting a phenol compound of the formula (II) with a phosphoric acid chloride of the formula (III) in the presence of an acid acceptor.

The above reaction is conducted in an organic solvent or in a two-phase mixture of an organic solvent and water. Examples of such organic solvent include ethers such as ethyl ether, butyl ether, tetrahydrofuran, dioxane, etc., nitriles such as acetonitrile, propionitrile, etc., ketones such as acetone, methyl ethyl ketone, etc., aromatic hydrocarbons such as benzene, toluene, etc., and halogenated hydrocarbons such as dichloromethane, dichloroethane, chloroform, carbon tetrachloride and so on. While the ratio of said phenol derivative of the formula (II) to said phosphoric acid chloride of the formula (III) is not critical but may be selected from a broad range, it is generally preferable to use about 0.5 to 2 moles, particularly about 1 to 1.5 moles, of the phosphoric acid chloride (III) per mole of the phenol derivative (II). The acid acceptor may be selected from a broad range of known compounds including tertiary amines such as triethylamine, pyridine, etc., alkali metal carbonates such as sodium carbonate, potassium carbonate, etc., alkali metal hydroxides such as sodium hydroxide, potassium hydroxide, etc., and alkali metal hydrides such as sodium hydride, potassium hydride and so on. The amount of said acid acceptor is generally about 1 to 2 moles and preferably about 1 to 1.2 moles per mole of compound (II). This reaction generally proceeds smoothly at 0° to 50° C. and generally goes to completion in about 1 to 5 hours.

The compound (III) used as the starting material in the above Reaction scheme 1 is a known compound and can be easily prepared or procured commercially at low cost. The other starting material, i.e., the compound (II) can also be produced easily by the known procedures, for example in accordance with the following Reaction scheme 2, Reaction scheme 3 or Reaction scheme 4.

REACTION SCHEME 2

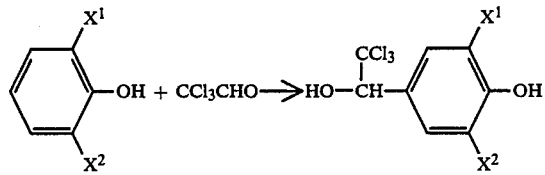

REACTION SCHEME 3

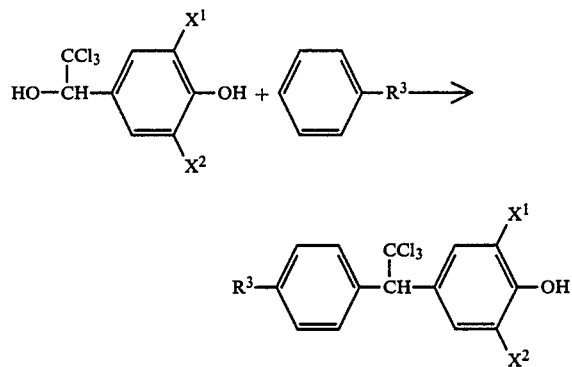

REACTION SCHEME 4

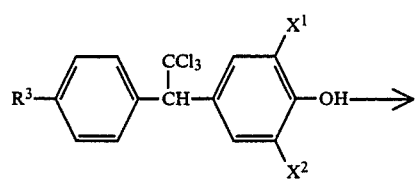

-continued

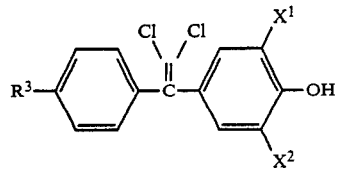

In the above formulas, $R^3$, $X^1$ and $X^2$ are as defined hereinbefore.

The reaction according to Reaction scheme 2 is conduced in the presence of a base such as potassium carbonate, and a detailed description of this reaction can be found in Japanese Unexamined Patent Publication (Kokai), No. 57-146736.

The reaction according to Reaction scheme 3 is conducted in the presence of an appropriate condensing agent such as sulfuric acid and a detailed description of this reaction can be found in the specification of U.S. Pat. No. 2766293.

The reaction according to Reaction scheme 4 is conducted in the presence of a base such as sodium hydroxide, sodium methoxide or the like and a detailed description of the reaction can be found in J. Pract. Chem., 323 (4), 637–646 (1981).

The compound of the present invention as produced by the method described hereinbefore can be easily isolated and purified from the reaction mixture by the conventional separatory procedures such as solvent extraction, solvent dilution, distillation, recrystallization, column chromatography and so on. In accordance with the above-described production method, the compound of the present invention can be produced in high yield and high purity.

The following is a partial listing of compounds according to the present invention.

O-ethyl S-n-propyl O-[4-(β,β-dichloro-α-phenyl)-vinyl]phenylphosphorothioate (Compound 1)

O-ethyl S-n-propyl O-{4-[β,β-dichloro-α-(p-methoxy)-phenyl]vinyl}phenylphosphorodithioate (Compound 2)

O-ethyl S-isobutyl O-[4-(β,β-dichloro-α-phenyl)vinyl]-phenylphosphorothioate (Compound 3)

O-ethyl S-n-propyl O-{4-[β,β-dichloro-α-(p-ethoxy)-phenyl]vinyl}phenylphosphorothioate (Compound 4)

O-ethyl S-n-propyl O-{4-[β,β-dichloro-α-(p-methyl)-phenyl]vinyl}phenylphosphorothioate (Compound 5)

O-ethyl S-n-propyl O-{4-[β,β-dichloro-α-(p-isopropyl)phenyl]vinyl}phenylphosphorothioate (Compound 6)

O-ethyl S-n-propyl O-[4-(β,β-dichloro-α-phenyl)-vinyl]-2-chlorophenylphosphorothioate (Compound 7)

O-ethyl S-n-propyl O-{4-[β,β-dichloro-α-(p-methoxy)-phenyl]vinyl}-2-chlorophenylphosphorothioate (Compound 8)

O-ethyl S-isobutyl O-{4-[β,β-dichloro-α-(p-methyl)-phenyl]vinyl}phenylphosphorothioate (Compound 9)

O-ethyl S-n-propyl O-[4-(β,β-dichloro-α-phenyl)-vinyl]-2,6-dichlorophenylphosphorothioate (Compound 10)

O-ethyl S-n-propyl O-[4-(β,β-dichloro-α-phenyl)-vinyl]-2,6-dibromophenylphosphorothioate (Compound 11)

O-ethyl S-isobutyl O-[4-(β,β-dichloro-α-phenyl)vinyl]-2,6-dichlorophenylphosphorothioate (Compound 12)

O-ethyl S-n-propyl O-{4-[β,β-dichloro-α-(p-chloro)phenyl]vinyl}-2,6-dichlorophenylphosphorothioate (Compound 13)

O-ethyl S-n-propyl O-{4-[β,β-dichloro-α-(p-methyl)phenyl]vinyl}-2,6-dichlorophenylphosphorothioate (Compound 14)

O-ethyl S-n-propyl O-{4-[β,β-dichloro-α-(p-isopropyl)phenyl]vinyl}-2,6-dichlorophenylphosphorothioate (Compound 15)

O-ethyl S-n-propyl O-{4-[β,β-dichloro-α-(p-methoxy)phenyl]vinyl}-2,6-dichlorophenylphosphorothioate (Compound 16)

O-ethyl S-isobutyl O-{4-[β,β-dichloro-α-(p-methoxy)phenyl]vinyl}-2,6-dichlorophenylphosphorothioate (Compound 17)

O-ethyl S-n-propyl O-{4-[β,β-dichloro-α-(p-ethoxy)phenyl]vinyl}-2,6-dichlorophenylphosphorothioate (Compound 18)

O-ethyl S-n-propyl O-{4-[β,β-dichloro-α-(p-methylthio)phenyl]vinyl}phenylphosphorodithioate (Compound 19)

O-ethyl S-n-propyl O-{4-[β,β-dichloro-α-(p-methylthio)phenyl]vinyl}-2,6-dichlorophenylphosphorothioate (Compound 20)

O-ethyl S-n-propyl O-{4-[β,β-dichloro-α-(p-ethyl)phenyl]vinyl}phenylphosphorothioate (Compound 21)

O-ethyl S-n-propyl O-[4-(β,β-dichloro-α-phenyl)vinyl]phenyldithiophosphate (Compound 22)

O-methyl S-n-propyl O-[4-(β,β-dichloro-α-phenyl)vinyl]phenylphosphorothioate (Compound 23)

O-methyl S-isobutyl O-[4-(β,β-dichloro-α-phenyl)vinyl]phenylphosphorothioate (Compound 24)

O-methyl S-n-propyl O-{4-[β,β-dichloro-α-(p-methoxy)phenyl]vinyl}phenylphosphorothioate (Compound 25)

O-methyl S-isobutyl O-{4-[β,β-dichloro-α-(p-methoxy)phenyl]vinyl}phenylphosphorothioate (Compound 26)

O-ethyl S-isobutyl O-{4-[β,β-dichloro-α-(p-methyl)phenyl]vinyl}phenylphosphorothioate (Compound 27)

O-methyl S-isobutyl O-[4-(β,β-dichloro-α-phenyl)vinyl]phenylphosphorodithioate (Compound 28)

The compound according to the present invention has strong miticidal activity, does not exterminate insects of the order Coleoptera such as ladybugs which are natural enemies of mites and features long residual activity and low toxicity to warm-blooded animals, so that it can be applied advantageously as a mite control agent for vegetables, orchard trees, and so on. Furthermore, the compound according to the present invention has insecticidal activity against noxious insects such as those of the order Lepidoptera, e.g. *Prodenia litura* Fabricius (common cutworm), *Plutella maculipennis* Curtis (diamond-back moth), *Adoxophyes orana* Fischer von Röslerstamm (smaller tea tortrix), etc., the order Hemiptera, e.g. aphids or plantlice, *Nephotetix cincticeps* Uhler (green rice leafhopper), etc. and the order Thysanoptera, e.g. thrips palmi, etc. and can therefore be used as an insecticidal agent or a miticidal agent possessing insecticidal activity against such noxious insects.

For use as an insectidal and/or miticidal agent, the compound according to the present invention can be made available in various application forms such as an emulsifiable concentrate, aqueous solution, suspension, fine dust, dust, wettable powder, paste, foamable spray composition, microencapsulated preparation, aerosol preparation, natural or synthetic matrix-imbibed preparation, fumigant composition, ultraflow volume concentrate, and so on. In the preparation of such application forms, various surfactants which are conventionally used in the art can be used for emulsifying, dispersing, suspending, and/or foaming purposes. Such surfactants include nonionic surfactants such as polyoxyethylene alkyl ethers, polyoxyethylene alkyl esters, polyoxyethylene sorbitan alkyl esters, sorbitan alkyl esters, etc., anionic surfactants such as alkyl benzenesulfonates, alkyl sulfosuccinates, alkyl sulfates, polyoxyethylene alkyl sulfates, aryl sulfonates, lignin sulfite, and so on. As said vehicle, diluent or carrier, various organic solvents, aerosol propellants, naturally-occurring mineral and vegetable materials, and synthetic compounds which are conventional in this field of art can be utilized. As preferred examples of said organic solvent, there may be mentioned benzene, toluene, xylene, ethylbenzene, chlorobenzene, alkylnaphthalenes, dichloromethane, chloroethylene, cyclohexane, cyclohexanone, acetone, methyl ethyl ketone, methyl isobutyl ketone, alcohols, dimethylformamide, dimethyl sulfoxide, acetonitrile, mineral oil fractions, and so on. The aerosol propellants include, among others, propane, butane, halogenated hydrocarbons, nitrogen, carbon dioxide and so on. The mineral materials include kaolin, talc, bentonite, diatomaceus earth, clay, montmorillonite, chalk, calcite, pumice, sepiolite, dolomite, and so on. The vegetable materials include walnut shells, tobacco stalks, sawdust and so on. Examples of said synthetic compounds include alumina, silicate, polysaccharides and so on. As adhesive agents, carboxymethylcellulose, gum arabic, polyvinyl alcohol, polyvinyl acetate, and so on may be employed. Furthermore, said various compositions may be tinted with an organic or inorganic colorant. In the various compositions provided by the present invention, the compound of the present invention may be incorporated in a proportion of about 0.1 to 95 weight percent and preferably about 0.5 to 90 weight percent.

Such compositions may be used as such or after dilution with a suitable carrier or a vehicle such as water to a concentration suited for the intended application. Thus, the dilution may contain about 0.00001 to 100 weight percent and, preferably, about 0.0001 to 10 weight percent of the compound of the present invention. The application amount varies with the severity of infestation with mites, etc., weather, and other conditions and cannot be generally specified. However, it should be a miticidally and/or insecticidally effective amount, and generally the composition of the present invention is used in an amount in the range of about 0.1 to 10 kg, preferably about 0.1 to 1 kg, per hectare, calculated as the compound of the formula (I).

The following examples and test examples are intended to illustrate the present invention in further detail.

EXAMPLE 1

To 20 ml of methylene chloride were added 2.65 g of 4-(β,β-dichloro-α-phenyl)vinylphenol and 1.05 g of triethylamine, and with stirring and ice-cooling, 2.03 g of O-ethyl S-n-propyl thiophosphoric chloride was added dropwise. After completion of dropwise addition, the mixture was stirred at room temperature for an additional hour. The reaction mixture was washed with 5% hydrochloric acid, 5% aqueous sodium hydrogen carbonate, and saturated aqueous solution of sodium chloride in the order mentioned, followed by drying over anhydrous magnesium sulfate. The solvent was then distilled off to give 4.10 g of O-ethyl S-propyl O-[4-(β,β-dichloro-α-phenyl)vinyl]phenyl phosphorothioate as a pale yellow oil.

IR (neat); 1260 cm$^{-1}$ (P=O).

NMR (CDCl$_3$); δppm; 0.8–1.80 (m, 8H, alkyl); 2.56–3.10 (m, 2H, CH$_2$S); 3.90–4.32 (m, 2H, CH$_2$O); 7.0–7.40 (m, 9H, aromatic H).

Based on the above physical data, the compound was identified as

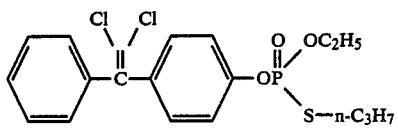

EXAMPLE 2

To 30 ml of acetonitrile were added 2.95 g of 4-[β,β-dichloro-α-(p-methoxy)phenyl]vinylphenol and 1.35 g of anhydrous potassium carbonate and the mixture was heated at 40° to 45° C. with stirring for 1 hour. After cooling to room temperature, 2.18 g of O-ethyl S-n-propyl dithiophosphoric chloride was added dropwise. The mixture was stirred at 50° to 60° C. for 4 hours, after which the precipitated salt was filtered off. The filtrate was concentrated and the residue was purified on a silica gel column (benzene-ethyl acetate=10:1) to give 5.25 g of O-ethyl S-n-propyl O-[4-[β,β-dichloro-α-(p-methoxy)phenyl]vinylphenyl]dithiophosphate as a pale yellow oil.

IR (neat); 663, 790 cm$^{-1}$ (P=S).

NMR (CDCl$_3$); δppm; 0.70–1.90 (m, 8H, alkyl); 2.60–3.15 (m, 2H, CH$_2$S); 3.90–4.30 (m, 2H, CH$_2$O); 3.80 (s, 3H, CH$_3$O); 6.68–7.38 (m, 8H, aromatic H).

Based on the above physical data, the compound was identified as

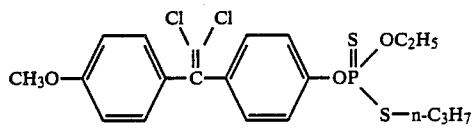

EXAMPLES 3 TO 28

In the same manner as Examples 1 and 2, the compounds listed in Table 1 were synthesized. The physical data on these compounds are also given in Table 1.

TABLE 1

| Example No. | Compound | Appearance | IR (neat) | NMR (CDCl$_3$) δ ppm |
|---|---|---|---|---|
| 3 | (Ph)C(Cl)$_2$=C–C$_6$H$_4$–OP(O)(OEt)(SBu$^{iso}$) | pale yellow oil | 1260 cm$^{-1}$ (P = O) | 0.9–2.30 (m, 10H, alkyl); 2.60–3.10 (m, 2H, CH$_2$S); 3.90–4.40 (m, 2H, CH$_2$O); 7.0–7.40 (br, 9H, aromatic H) |
| 4 | EtO–C$_6$H$_4$–C(=CCl$_2$)–C$_6$H$_4$–OP(O)(OEt)(SPr$^n$) | yellow oil | 1260 cm$^{-1}$ (P = O) | 0.78–2.0 (m, 11H, alkyl); 2.50–3.0 (m, 2H, CH$_2$S); 3.62–4.30 (m, 4H, CH$_2$O); 6.58–7.40 (m, 8H, aromatic H) |
| 5 | Me–C$_6$H$_4$–C(=CCl$_2$)–C$_6$H$_4$–OP(O)(OEt)(SPr$^n$) | pale yellow oil | 1260 cm$^{-1}$ (P = O) | 0.8–2.0 (m, 8H, alkyl); 2.20 (s, 3H, CH$_3$–C); 2.60–3.10 (m, 2H, CH$_2$S); 3.90–4.40 (m, 2H, CH$_2$O); 6.6–7.40 (m, 8H, aromatic H) |
| 6 | Pr$^{iso}$–C$_6$H$_4$–C(=CCl$_2$)–C$_6$H$_4$–OP(O)(OEt)(SPr$^n$) | pale yellow oil | 1260 cm$^{-1}$ (P = O) | 0.70–2.0 (m, 14H, alkyl); 2.68 (m, 1H, CH–C); 2.70–3.20 (m, 2H, CH$_2$S); 3.90–4.40 (m, 2H, CH$_2$O); 6.6–7.40 (m, 8H, aromatic H) |
| 7 | Ph–C(=CCl$_2$)–C$_6$H$_3$(Cl)–OP(O)(OEt)(SPr$^n$) | pale yellow oil | 1260 cm$^{-1}$ (P = O) | 0.70–1.90 (m, 8H, alkyl); 2.68–3.16 (m, 2H, CH$_2$S); 3.96–4.48 (m, 2H, CH$_2$O); 6.60–7.42 (m, 8H, aromatic H) |
| 8 | MeO–C$_6$H$_4$–C(=CCl$_2$)–C$_6$H$_3$(Cl)–OP(O)(OEt)(SPr$^n$) | yellow oil | 1260 cm$^{-1}$ (P = O) | 0.70–1.90 (m, 8H, alkyl); 2.68–3.16 (m, 2H, CH$_2$S); 3.60 (s, 3H, CH$_3$O); 3.96–4.48 (m, 2H, CH$_2$O); 6.62–7.44 (m, 7H, aromatic H) |

TABLE 1-continued

| Example No. | Compound | Appearance | IR (neat) | NMR (CDCl$_3$) δ ppm |
|---|---|---|---|---|
| 9 | 4-Me-C$_6$H$_4$–C(=CCl$_2$)–C$_6$H$_4$–O–P(=O)(OEt)(SBu$^{iso}$) | yellow oil | 1260 cm$^{-1}$ (P=O) | 0.70–2.1 (m, 10H, alkyl)<br>2.20 (s, 3H, CH$_3$–C)<br>2.70–3.20 (m, 2H, CH$_2$S)<br>3.90–4.40 (m, 2H, CH$_2$O)<br>6.70–7.40 (m, 8H, aromatic H) |
| 10 | C$_6$H$_5$–C(=CCl$_2$)–(2,6-Cl$_2$-C$_6$H$_2$)–O–P(=O)(OEt)(SPr$^n$) | pale yellow oil | 1260 cm$^{-1}$ (P=O) | 0.7–1.9 (m, 8H, alkyl)<br>2.68–3.16 (m, 2H, CH$_2$S)<br>3.96–4.48 (m, 2H, CH$_2$O)<br>7.1–7.3 (br, 7H, aromatic H) |
| 11 | C$_6$H$_5$–C(=CCl$_2$)–(2,6-Br$_2$-C$_6$H$_2$)–O–P(=O)(OEt)(SPr$^n$) | pale yellow oil | 1260 cm$^{-1}$ (P=O) | 0.7–1.9 (m, 8H, alkyl)<br>2.68–3.16 (m, 2H, CH$_2$S)<br>3.96–4.48 (m, 2H, CH$_2$O)<br>7.1–7.3 (m, 7H, aromatic H) |
| 12 | C$_6$H$_5$–C(=CCl$_2$)–(2,6-Cl$_2$-C$_6$H$_2$)–O–P(=O)(OEt)(SBu$^{iso}$) | pale yellow oil | 1260 cm$^{-1}$ (P=O) | 0.7–1.98 (m, 10H, alkyl)<br>2.70–3.20 (m, 2H, CH$_2$S)<br>3.96–4.48 (m, 2H, CH$_2$O)<br>7.08–7.14 (m, 7H, aromatic H) |
| 13 | 4-Cl-C$_6$H$_4$–C(=CCl$_2$)–(2,6-Cl$_2$-C$_6$H$_2$)–O–P(=O)(OEt)(SPr$^n$) | yellow oil | 1260 cm$^{-1}$ (P=O) | 0.8–2.0 (m, 8H, alkyl)<br>2.68–3.16 (m, 2H, CH$_2$S)<br>3.96–4.48 (m, 2H, CH$_2$O)<br>6.98–7.42 (m, 6H, aromatic H) |
| 14 | 4-Me-C$_6$H$_4$–C(=CCl$_2$)–(2,6-Cl$_2$-C$_6$H$_2$)–O–P(=O)(OEt)(SPr$^n$) | yellow oil | 1260 cm$^{-1}$ (P=O) | 0.8–2.0 (m, 8H, alkyl)<br>2.20 (s, 3H, CH$_3$–C)<br>2.70–3.20 (m, 2H, CH$_2$S)<br>3.90–4.40 (m, 2H, CH$_2$O)<br>7.0–7.40 (m, 6H, aromatic H) |
| 15 | 4-Pr$^{iso}$-C$_6$H$_4$–C(=CCl$_2$)–(2,6-Cl$_2$-C$_6$H$_2$)–O–P(=O)(OEt)(SPr$^n$) | yellow oil | 1260 cm$^{-1}$ (P=O) | 0.70–2.0 (m, 14H, alkyl)<br>2.68 (m, 1H, CH–C)<br>2.70–3.20 (m, 2H, CH$_2$S)<br>3.90–4.40 (m, 2H, CH$_2$O)<br>7.0–7.40 (m, 6H, aromatic H) |
| 16 | 4-MeO-C$_6$H$_4$–C(=CCl$_2$)–(2,6-Cl$_2$-C$_6$H$_2$)–O–P(=O)(OEt)(SPr$^n$) | yellow oil | 1260 cm$^{-1}$ (P=O) | 0.7–1.9 (m, 8H, alkyl)<br>2.68–3.16 (m, 2H, CH$_3$S)<br>3.62 (s, 3H, CH$_3$O)<br>3.96–4.48 (m, 2H, CH$_2$O)<br>6.68–7.38 (m, 6H, aromatic H) |
| 17 | 4-MeO-C$_6$H$_4$–C(=CCl$_2$)–(2,6-Cl$_2$-C$_6$H$_2$)–O–P(=O)(OEt)(SBu$^{iso}$) | yellow oil | 1260 cm$^{-1}$ (P=O) | 0.7–1.90 (m, 10H, alkyl)<br>2.70–3.15 (m, 2H, CH$_2$S)<br>3.68 (s, 3H, CH$_3$O)<br>3.96–4.40 (m, 2H, CH$_2$O)<br>6.70–7.36 (m, 6H, aromatic H) |

TABLE 1-continued

| Example No. | Compound | Appearance | IR (neat) | NMR (CDCl₃) δ ppm |
|---|---|---|---|---|
| 18 | EtO-C₆H₄-C(=CCl₂)-C₆H₂Cl₃-O-P(=O)(OEt)(SPr<sup>n</sup>) | yellow oil | 1260 cm⁻¹ (P=O) | 0.72–1.9 (m, 11H, alkyl)<br>2.68–3.16 (m, 2H, CH₂S)<br>3.62–4.30 (m, 4H, CH₂O)<br>6.70–7.40 (m, 6H, aromatic H) |
| 19 | MeS-C₆H₄-C(=CCl₂)-C₆H₄-O-P(=S)(OEt)(SPr<sup>n</sup>) | pale yellow oil | 663, 790 cm⁻¹ (P=S) | 0.7–1.9 (m, 8H, alkyl)<br>2.36 (s, 3H, CH₃S)<br>2.70–3.20 (m, 2H, CH₂S)<br>3.96–4.48 (m, 2H, CH₂O)<br>6.90–7.50 (m, 8H, aromatic H) |
| 20 | MeS-C₆H₄-C(=CCl₂)-C₆H₂Cl₂-O-P(=O)(OEt)(SPr<sup>n</sup>) | pale yellow oil | 1260 cm⁻¹ (P=O) | 0.70–1.90 (m, 8H, alkyl)<br>2.36 (s, 3H, CH₃S)<br>2.68–3.16 (m, 2H, CH₂S)<br>4.0–4.52 (m, 2H, CH₂O)<br>6.98–7.42 (m, 6H, aromatic H) |
| 21 | Et-C₆H₄-C(=CCl₂)-C₆H₄-O-P(=O)(OEt)(SPr<sup>n</sup>) | pale yellow oil | 1260 cm⁻¹ (P=O) | 0.70–1.9 (m, 11H, alkyl)<br>2.50 (m, 2H, CH₂—C)<br>2.70–3.20 (m, 2H, CH₂S)<br>3.90–4.40 (m, 2H, CH₂O)<br>6.90–7.40 (m, 8H, aromatic H) |
| 22 | C₆H₅-C(=CCl₂)-C₆H₄-O-P(=S)(OEt)(SPr<sup>n</sup>) | yellow oil | 663, 790 cm⁻¹ (P=S) | 0.90–1.98 (m, 8H, alkyl)<br>2.70–3.15 (m, 2H, CH₂S)<br>3.70–4.40 (m, 2H, CH₂O)<br>6.98–7.40 (m, 9H, aromatic H) |
| 23 | C₆H₅-C(=CCl₂)-C₆H₄-O-P(=O)(OMe)(SPr<sup>n</sup>) | pale yellow oil | 1260 cm⁻¹ (P=O) | 0.9–2.0 (m, 5H, alkyl)<br>2.66–3.20 (m, 2H, CH₂S)<br>3.82 (d, 3H, CH₃O)<br>6.98–7.4 (m, 9H, aromatic H) |
| 24 | C₆H₅-C(=CCl₂)-C₆H₄-O-P(=O)(OMe)(SBu<sup>iso</sup>) | pale yellow oil | 1260 cm⁻¹ (P=O) | 0.96–2.20 (m, 7H, alkyl)<br>2.70–3.15 (m, 2H, CH₂S)<br>3.68 (d, 3H, CH₃O)<br>6.98–7.40 (m, 9H, aromatic H) |
| 25 | MeO-C₆H₄-C(=CCl₂)-C₆H₄-O-P(=O)(OMe)(SPr<sup>n</sup>) | yellow oil | 1260 cm⁻¹ (P=O) | 0.9–2.0 (m, 5H, alkyl)<br>2.66–3.20 (m, 2H, CH₂S)<br>3.60 (s, 3H, CH₃O)<br>3.70 (d, 3H, CH₃O)<br>6.60–7.40 (m, 8H, aromatic H) |
| 26 | MeO-C₆H₄-C(=CCl₂)-C₆H₄-O-P(=O)(OMe)(SBu<sup>iso</sup>) | yellow oil | 1260 cm⁻¹ (P=O) | 0.9–2.2 (m, 7H, alkyl)<br>2.70–3.15 (m, 2H, CH₂S)<br>3.60 (s, 3H, CH₃O)<br>3.70 (d, 3H, CH₃O)<br>6.62–7.40 (m, 8H, aromatic H) |
| 27 | Me-C₆H₄-C(=CCl₂)-C₆H₄-O-P(=O)(OEt)(SBu<sup>iso</sup>) | yellow oil | 1260 cm⁻¹ (P=O) | 0.7–2.20 (m, 10H, alkyl)<br>2.22 (s, 3H, CH₃—C)<br>2.70–3.20 (m, 2H, CH₂S)<br>3.90–4.40 (m, 2H, CH₂O)<br>6.60–7.40 (m, 8H, aromatic H) |
| 28 | C₆H₅-C(=CCl₂)-C₆H₄-O-P(=S)(OMe)(SBu<sup>iso</sup>) | yellow oil | 663, 790 cm⁻¹ (P=S) | 0.96–2.20 (m, 7H, alkyl)<br>2.70–3.15 (m, 2H, CH₂S)<br>3.70 (d, 3H, CH₃—O)<br>6.98–7.38 (m, 9H, aromatic H) |

In Table 1, "Me" represents methyl, "Et" represents ethyl, "Pr$^n$" represents n-propyl, "Pr$^{iso}$" represents isopropyl and "Bu$^{iso}$" represents isobutyl.

TEST EXAMPLE 1

(two-spotted spider mites)

In 98 weight parts of acetone was dissolved 2 weight parts of the compound according to the present invention. This solution was diluted with water containing 0.04% of a spreader and sticker (Trademark "Shinrino", product of Nihon Nohyaku Co., Ltd.) to a predetermined concentration. Kidney-bean plants in pots were inoculated with adult two-spotted spider mites (*Tetranychus urticae* Koch) and the above dilution was sprayed until it dripped. The mortality was investigated 3 days later. The results are shown in Table 2. The test compound No. in Table 2 corresponds to Example No.

TABLE 2

| Test Compound No. | Concentration of Test Compound (%) | Mortality (%) |
|---|---|---|
| 1 | 0.02 | 100 |
|   | 0.005 | 100 |
| 3 | 0.02 | 100 |
|   | 0.005 | 100 |
| 4 | 0.02 | 100 |
|   | 0.005 | 100 |
| 5 | 0.02 | 100 |
|   | 0.005 | 100 |
| 9 | 0.02 | 100 |
|   | 0.005 | 100 |
| 10 | 0.02 | 100 |
|   | 0.005 | 100 |
| 13 | 0.02 | 100 |
|   | 0.005 | 100 |
| 19 | 0.02 | 100 |
|   | 0.005 | 100 |
| 23 | 0.02 | 100 |
|   | 0.005 | 100 |
| 25 | 0.02 | 100 |
|   | 0.005 | 100 |
| 27 | 0.02 | 100 |
|   | 0.005 | 100 |
| A | 0.02 | 100 |
|   | 0.005 | 70 |

A: Kelthane (comparative compound)

TEST EXAMPLE 2

(aphids)

In 98 weight parts of acetone was dissolved 2 weight parts of the compound according to the present invention. This solution was diluted to a predetermined concentration with water containing 0.04% of a spreader and sticker (Trademark "Shinrino", product of Nihon Nohyaku Co., Ltd.). Cucumber seedlings (2- to 3-leaf stage) in pots were inoculated with 10 cotton aphids (*Aphis gossypii* Glover) per pot and after 2 days, the above dilution was sprayed. The population of infesting aphids was counted 7 days after application of the chemical and compared with the population in the control group to find the mortality. The results are shown in Table 3. The test compound No. in Table 3 corresponds to Example No.

TABLE 3

| Test Compound No. | Concentration of Test Compound (ppm) | Mortality (%) |
|---|---|---|
| 3 | 100 | 90 |
|   | 300 | 100 |
| 4 | 100 | 85 |
|   | 300 | 100 |
| 5 | 100 | 85 |
|   | 300 | 100 |
| 8 | 100 | 96 |
|   | 300 | 100 |
| 9 | 100 | 80 |
|   | 300 | 100 |
| 10 | 100 | 90 |
|   | 300 | 100 |
| 13 | 100 | 88 |
|   | 300 | 100 |
| 14 | 100 | 84 |
|   | 300 | 100 |
| 19 | 100 | 70 |
|   | 300 | 100 |
| 20 | 100 | 80 |
|   | 300 | 100 |

TEST EXAMPLE 3

(thrips palmi)

In 98 weight parts of acetone was dissolved 2 weight parts of the compound according to the present invention. This solution was diluted to a predetermined concentration with water containing 0.04% of a spreader and sticker (Trademark "Shinrino", product of Nihon Nohyaku Co., Ltd.). Cucumber seedlings (2- to 3-leaf stage) in pots were inoculated with 10 thrips palmi and 2 days after their release, the above dilution was sprayed. The population of parasitic thrips was counted 7 days after application of the chemical and compared with the control group population to find the mortality. The results are shown in Table 4. The test compound No. in Table 4 corresponds to Example No.

TABLE 4

| Test Compound No. | Concentration of Test Compound (ppm) | Mortality (%) |
|---|---|---|
| 1 | 100 | 84 |
|   | 300 | 100 |
| 4 | 100 | 70 |
|   | 300 | 100 |
| 7 | 100 | 78 |
|   | 300 | 100 |
| 11 | 100 | 80 |
|   | 300 | 100 |
| 12 | 100 | 94 |
|   | 300 | 100 |
| 15 | 100 | 80 |
|   | 300 | 100 |
| 16 | 100 | 83 |
|   | 300 | 100 |
| 18 | 100 | 78 |
|   | 300 | 100 |
| 21 | 100 | 86 |
|   | 300 | 100 |
| 26 | 100 | 90 |
|   | 300 | 100 |

TEST EXAMPLE 4

(diamond-back moth)

In 98 weight parts of acetone was dissolved 2 weight parts of the compound according to the present invention. This solution was diluted to a predetermined concentration with water containing 0.04% of a spreader and sticker (Trademark "Shinrino", product of Nihon Nohyaku Co., Ltd.). Cabbage seedlings in pots were inoculated with 10 third-instar larva of diamond-back moth per pot and the above dilution was sprayed. The population of infesting larva was counted 3 days after application of the chemical and compared with the population in the control group to find the mortality. The results are shown in Table 5. The test compound No. in Table 5 corresponds to Example No.

TABLE 5

| Test Compound No. | Concentration of Test Compound (ppm) | Mortality (%) |
|---|---|---|
| 1 | 100 | 75 |
|   | 300 | 92 |
| 2 | 100 | 70 |
|   | 300 | 88 |
| 5 | 100 | 80 |
|   | 300 | 95 |
| 7 | 100 | 90 |
|   | 300 | 100 |
| 13 | 100 | 88 |
|   | 300 | 100 |
| 15 | 100 | 85 |
|   | 300 | 100 |
| 19 | 100 | 70 |
|   | 300 | 85 |
| 21 | 100 | 70 |
|   | 300 | 80 |
| 24 | 100 | 75 |
|   | 300 | 90 |
| 25 | 100 | 70 |
|   | 300 | 89 |

What is claimed is:

1. A phosphoric ester derivative of the formula (I):

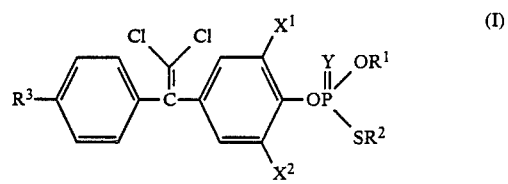

wherein $R^1$ and $R^2$ each represents a lower alkyl group; $R^3$ represents a hydrogen atom, a halogen atom, a lower alkyl group, a lower alkoxy group or a lower alkylthio group; $X^1$ and $X^2$ are the same or different and each represents a hydrogen atom or a halogen atom; and Y represents an oxygen atom or a sulfur atom.

2. An insecticidal and miticidal composition comprising an effective amount of at least one species of the phosphoric ester derivative of the formula:

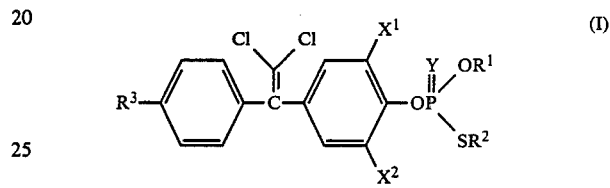

wherein $R^1$ and $R^2$ each represents a lower alkyl group; $R^3$ represents a hydrogen atom, a halogen atom, a lower alkyl group, a lower alkoxy group or a lower alkylthio group; $X^1$ and $X^2$ are the same or different and each represents a hydrogen atom or a halogen atom; and Y represents an oxygen atom or a sulfur atom, and a vehicle, diluent or carrier thereof.

* * * * *